United States Patent [19]

Majid et al.

[11] Patent Number: 5,070,081

[45] Date of Patent: Dec. 3, 1991

[54] INCLUSION COMPLEXES OF CYCLODEXTRINS BY AGGLOMERATION

[75] Inventors: Abdul Majid, Ottawa; John A. Ripmeester, Gloucester, both of Canada

[73] Assignee: National Research Council of Canada, Ottawa, Canada

[21] Appl. No.: 337,969

[22] Filed: Apr. 14, 1989

[30] Foreign Application Priority Data

Apr. 20, 1988 [CA] Canada ................................ 564609

[51] Int. Cl.$^5$ ................ A61K 9/62; A61K 31/70; B01J 13/02
[52] U.S. Cl. .................................. 514/58; 536/103; 514/778; 514/974; 512/4
[58] Field of Search .............. 514/58, 778, 974; 536/103; 512/4

[56] References Cited

U.S. PATENT DOCUMENTS

| | | | |
|---|---|---|---|
| 4,438,106 | 3/1984 | Wagu et al. | 536/103 |
| 4,575,548 | 3/1986 | Ueda et al. | 536/103 |
| 4,675,395 | 6/1987 | Fukazawa et al. | 536/103 |
| 4,834,985 | 5/1989 | Elger et al. | 536/103 |
| 4,904,773 | 2/1990 | Yu et al. | 536/103 |
| 4,916,161 | 4/1990 | Patell | 514/781 |

FOREIGN PATENT DOCUMENTS 186146  7/1986  European Pat. Off. .

OTHER PUBLICATIONS

M. Kurozumi et al., "Inclusion Compounds of Non-Steroidal Antiinflammatory and Other Slightly Soluble Drugs with α-and β-Cyclodextrins in Powdered Form", Chem. Pharm. Bull. 23 (12), 3062-3068 (1975).

*Primary Examiner*—Ronald W. Griffin
*Attorney, Agent, or Firm*—Alan A. Thomson

[57] ABSTRACT

A combined process is described in which inclusion complexes are formed from guest molecules and cyclodextrins during agglomeration of the cyclodextrins. Sufficient agitation in the presence of a small amount of water results in complex formation and bonding into strong agglomerates. The agglomerates are strong and stable and useful *inter alia* in foods (the guest molecules are flavors), pharmaceuticals (the guest molecules are drugs) and agriculture (the guest molecules are various agrochemicals).

12 Claims, No Drawings

INCLUSION COMPLEXES OF CYCLODEXTRINS BY AGGLOMERATION

This invention is concerned with the formation of agglomerates of cyclodextrin inclusion complexes directly from guest molecule materials and cyclodextrins. The resulting agglomerates have been found to be strong, stable and easily handled.

Cyclodextrins, discovered about one century ago, are emerging as a new group of industrial materials. The ability to include a variety of guest molecules into their hydrophobic cavity, without the formation of any covalent bond, is their most important property. Among the natural cyclodextrins, $\beta$-cyclodextrin is widely used because of its unique cavity size (internal diameter about 6.5 Å), and the ease with which it can be obtained on a large scale.

The guest inclusion function of cyclodextrins has been adopted for pharmaceuticals, foods, cosmetics, toiletries, agrochemicals, and other industrial uses. Many basic studies on cyclodextrins have been published, covering artificial enzymes, catalysts, photocontrolled reactions, isomer separation or selective production, and molecular electronics.

Some of the advantages and uses of cyclodextrin guest complexation include:

(1) Stabilization, controlled release and storage as stable powders of gaseous, volatile, and sublimable guest substances, e.g. pesticides.

(2) Improvement of physical and chemical stability of labile compounds e.g. these guest compounds are protected from oxidation by air; the rates of decomposition, disproportionation, polymerization, autocatalytic reactions, etc. are considerably decreased and sensitivity to light is reduced.

(3) In the formulation of drugs, liquid guest compounds can be transformed into a solid form which is suitable for tablet-manufacturing. Usually bad tastes or smells can be masked, and incompatible compounds can be mixed when one of the components is protected by inclusion complex formation.

(4) The bioavailability of poorly soluble drugs can be enhanced. The solubility in water, as well as the rate of dissolution of poorly soluble substances can be increased. Following oral administration of poorly water soluble drugs, higher blood levels can be achieved if they are complexed with cyclodextrins.

(5) A very promising method for the stabilization of food flavors and fragrances is their complexation with cyclodextrins, which has already been realized on an industrial scale.

(6) Unpleasant tastes and odors can be removed by cyclodextrin complexation. Thus, cyclodextrin complexation have been used for reducing the bitterness of orange and grapefruit juice, animal and plant protein hydrolysates, mushroom extracts, certain stereoisomers, and propylene glycol. It can lighten specific smells of mutton, fish meat, yeast extracts, soybean milk, fish meal, lecithin, and old grains.

(7) Separation, concentration and fractionation of specific substances. Separations of xylene isomers and ethylbenzenes, trimethylbenzenes, isomeric alkylphenols, alkyltoluene isomers, straight and branched chain hydrocarbons have been reported. Resolution of various enantiomers employing cyclodextrin complexation has also been reported.

Various known methods used for the formation of cyclodextrin complexes include: kneading, freeze drying, spray drying, mixed pulverization and crystallization from saturated solution. However, most of these methods are time consuming and laborious.

We have found that inclusion complexes with $\alpha$, $\beta$ or $\gamma$ cyclodextrins can be conveniently made in more advantageous form using agglomeration techniques. The advantages of this method and product include:

(1) It is more simple and quick than known methods.

(2) Complexation and agglomeration occur simultaneously thus eliminating an extra step for pelletization after complex formation.

(3) When the guest molecule is liquid, cyclodextrins can be dispersed in the liquid guest molecule phase, thus eliminating the need for a solvent.

(4) Agglomerates can be easily separated from the bulk liquid phase, e.g. by screening.

(5) The size of agglomerates can be controlled at will.

(6) The resulting agglomerates or pellets are strongly bonded by residual water remaining after drying and are very stable.

SUMMARY OF THE INVENTION

This invention includes a process for preparing inclusion complexes of guest molecules and cyclodextrins, in agglomerate form, comprising:

(a) contacting the cyclodextrin in solid form with a selected guest molecule material in the presence of a small amount of water sufficient to serve as agglomeration binding liquid, to form a mixture, (b) agitating the mixture sufficiently to cause interpenetration of the components and inclusion complex formation to occur, (c) continuing agitation until agglomerates form, and (d) recovering agglomerates of the inclusion complexes.

When the guest molecule material is a water-immiscible liquid, sufficient may be used to form a continuous liquid phase, and the agglomeration follows spherical agglomeration techniques (see A. F. Sirianni et al, Can. J. Chem. Engin. 1969, 47, 166-170). If the guest molecule is too viscous, an operative lower viscosity can be achieved by the addition of a water-immiscible solvent, e.g. hexane and diethylether.

When the guest material is solid, the steps include intimate solid-solid mixing and wet pelletization operations. In this case the guest material preferably is present in approximately the stoichiometric amount to form the desired inclusion complex. A stage of severe agitation has been found necessary to form the inclusion complex (with mild agitation the complex did not form). Any final wet pelletization procedure may be used to form the final agglomerates.

The amount of water added normally will be within about 10 to about 100% by wt. based on the cyclodextrin, preferably about 25-50%. Added water has been found necessary for formation of the complex and for agglomeration.

Excess liquid guest phase, after removal of the agglomerates, can be recycled to step (a).

The starting cyclodextrin can be any of the alpha, beta or gamma forms known in the art. Normally the form of cyclodextrin is used which has a cavity size matched to the size of the guest molecule. The match need not be exact. Usually the cyclodextrin will contain some water of hydration; additional water as outlined above is essential both for inclusion complex and for agglomerate formation.

Many different guest materials which will form the inclusion complexes may be used. Examples of guest liquids include citral, citronellal, limonene, peppermint oil, lemon oil, benzaldehyde, allethrins, and pyrethroids. Examples of guest solids include salicylic acid, cinnarizine, chloropicrin, and phenacetin. Tetrahydrocannabinol is a viscous liquid (see Example 5).

The resulting agglomerates are easily separated, recovered, handled and utilized. Not all of the added water is removed on drying: it appears some residual water is binding the cyclodextrin particles together. Under appropriate conditions the agglomerates are readily dispersed, dissolved or otherwise incorporated or applied.

The size of the agglomerates can be varied by controlling the amount of water added and to a lesser degree the agitation. Increasing the amount of water tends to increase the agglomerate size. Increasing the agitation tends to decrease the agglomerate size.

When the guest materials are water-soluble solids, wet pelletization techniques including a severe agitation, may be used to form the agglomerates.

The following examples will serve to illustrate the invention. Examples 1-3 involve liquid guest compounds and for these small scale tests the general procedure was as follows:

About 0.2-0.5 gms of hydrated β-cyclodextrin was dispersed in 2-5 ml of liquid guest compound in 250 ml glass jar. A small amount of water (50-500 microliter) was added to this suspension. The jar was sealed tightly using a polyethylene gasket. The contents were agitated on a Spex (TM) mixer for 5-15 minutes when agglomerates of β-cyclodextrin complex with the guest molecules were formed. This mixer gave a severe agitation in a 3-dimensional path to the jar contents. These agglomerates ranged in size from less than 0.1 mm to greater than 1 cm. Agglomerates were separated from excess guest compound either by decantation or by screening. Agglomerates were further dried by pressing against tissue papers. Complete drying of the agglomerates was not found to be necessary because the solid state CP/MAS, $^{13}$C NMR spectroscopy used for analytical characterization of the complexes only detects the complexed guest molecules. However, if complete removal of free guest compound from the agglomerates is necessary well established routine procedures such as spray drying, freeze drying and vacuum drying could be used.

Analytical Procedure: β-cyclodextrin complexes were characterized using solid state $^{13}$C NMR spectrometry. Spectra were obtained at 45.28 MHz on a Bruker CXP 180 NMR spectrometer using the cross polarization (CP) technique with magic angle spinning (MAS). A contact time of 2 ms and repetition times of 2-4S were selected. The magic angle spinning speeds were 3.0-4.0 KHz.

EXAMPLE 1

0.5 g of hydrated β-cyclodextrin was dispersed in 5 g of citral in a 250 ml glass jar. 100 microliters of water was added to this suspension and the contents agitated on a Spex (TM) mixer for 10 minutes. This resulted in the formation of micro-agglomerates of about 1 mm size. Excess citral was removed by decantation and agglomerates dried by pressing against tissue paper.

The CP/MAS, $^{13}$C NMR spectrum of these agglomerates was compared with the spectrum of hydrated β-cyclodextrin. A comparison of the two spectra clearly showed significant broadening of the carbon resonances of the β-cyclodextrin. This broadening is because of the displacement of water molecules in the host cavity by the citral molecules, indicating the formation of an inclusion complex. The guest molecule's resonances observed in the solid state complex were readily assigned due to their close resemblance to those observed in solution. It is interesting to note that the intensity of the C-5 signal of the cis isomer of citral was low compared with the C-5 signal of the corresponding trans isomer. Since, the starting guest material had almost equal proportions of both cis and trans isomers, this suggested selective complexation of the trans isomer compared with the cis isomer. This is consistent with published reports for the selective inclusion of a particular isomer of various guest materials. Inclusion complex formation has been employed in the separation of isomers.

EXAMPLE 2

0.65 g of hydrated β-cyclodextrin was dispersed in 5 g of citronellal in a glass jar. 100 microliters of water was added to this suspension and the contents agitated on a Spex (TM) mixer for 5 minutes. This gave 0.5-2 mm size agglomerates that were dried as described in Example 1.

The verification of the inclusion complex formation was obtained by comparing the CP/MAS-$^{13}$C NMR spectrum of these agglomerates with the hydrated β-cyclodextrin spectrum and the fact that all carbons from citronellal could be accounted for.

EXAMPLE 3

0.5 g of hydrated β-cyclodextrin was dispersed in 7 g of limonene. 100 microliters of water was added to this suspension and the contents agitated on a Spex (TM) mixer for 10 minutes. Microagglomerates of about 1 mm size were obtained that were dried as described in Example 1.

The formation of β-cyclodextrin-limonene complex was confirmed from the CP/MAS-$^{13}$C NMR spectrum of the agglomerates.

Wet pelletization has been carried out with three solid guest molecules to form the inclusion complex as agglomerates. One procedure is given in Example 4.

EXAMPLE 4

0.3-0.4 millimoles of the hydrated β-cyclodextrin and 0.5-0.8 millimoles of solid guest molecule were ground together in an agate pestle and mortar in the presence of 50-500 microliters (preferably 100-300 microliters) of water. The resulting paste was transferred to a 100 ml Teflon (TM) jar with a screw type cap and a rubber ring for a tight seal. After sealing the jar tightly the contents were agitated on a Spex (TM) mixer for 5-15 minutes when agglomerates of β-cyclodextrin complex with the guest molecules were formed. These agglomerates ranged in size from <0.1 mm to >0.2 mm. These complexes were characterized using solid state $^{13}$C NMR spectroscopy as described previously. Examples of solid guest molecules for which β-cyclodextrin complexes were prepared using this procedure include: salicylic acid, cinnarizine and phenacetin.

It is possible to form the complex and agglomerate using viscous liquid guest molecule material and cyclodextrin by dissolving the guest material in a water-immiscible solvent, adding the cyclodextrin and water and agitating as a slurry. Example 5 is typical.

EXAMPLE 5

Tetrahydrocannabinol (THC) was obtained as a solution in ethanol. The ethanol was evaporated and 0.1 g of THC was dissolved in 15 ml of hexane. $\beta$-cyclodextrin hydrate 0.2 g and 50 microliters of water were dispersed in the hexane solution, and the mixture agitated in a Spex (TM) mixer for 5–10 minutes. The resulting agglomerates were separated and dried. The dried agglomerates were free of hexane. Inclusion complex formation was confirmed as in Example 1.

Where the guest molecules are gaseous, it is possible to disperse the cyclodextrin particle in a water-immiscible liquid, add the water required for inclusion complex formation and agglomeration, and dissolve a stoichiometric excess of the gaseous guest molecules in the liquid phase before agitation. On appropriate agitation, agglomerates of the inclusion complexes will form. Examples include gaseous aromas or deodorizers.

We claim:

1. A process for preparing inclusion complexes of guest molecules and cyclodextrins, in agglomerate form, comprising:
   a) contacting the cyclodextrin in solid particulate form with a selected guest molecule material in the presence of a small amount of water only sufficient to serve as agglomeration binding liquid, to form a mixture,
   b) agitating the mixture sufficiently to cause interpenetration of the components and inclusion complex formation to occur,
   c) continuing agitation until agglomerates form,
   and d) recovering agglomerates of the inclusion complexes.

2. The process of claim 1 in which the guest material is liquid and sufficient is used to form a continuous liquid phase.

3. The process of claim 1 in which the guest material is solid and the steps include intimate solid-solid mixing and wet pelletization.

4. The process of claim 3 in which the guest material is present in approximately the stoichiometric amount to form the desired complex.

5. The process of claim 1 in which the amount of water is from about 10 to about 100% by wt. based on the cyclodextrin.

6. The process of claim 2 wherein after removal of the agglomerates, the excess liquid guest phase is recycled.

7. The process of claim 1 in which the recovered agglomerates are dried to remove unbound water and any excess liquid guest material.

8. The process of claim 1 in which the starting cyclodextrin comprises a hydrated beta-cyclodextrin.

9. The process of claim 2 in which the liquid guest material is selected from flavours, perfumes, agrochemicals, and drugs.

10. The process of claim 3 in which the solid guest material is selected from pharmaceuticals.

11. The process of claim 1 in which the guest material is gaseous, a water-immiscible liquid is present and an excess of the gaseous guest molecules are dissolved in the liquid phase in step (a).

12. Agglomerates of guest inclusion complexes of cyclodextrins formed by substantially concurrent complex formation and agglomeration, and containing bound water.

* * * * *